United States Patent
Matsuzaki

(10) Patent No.: US 8,746,037 B2
(45) Date of Patent: Jun. 10, 2014

(54) ULTRASONIC APPARATUS AND METHOD FOR MEASURING THE CONCENTRATION OF GAS

(75) Inventor: Taiga Matsuzaki, Yamaguchi (JP)

(73) Assignee: Teijin Pharma Limited, Tokyo (JP)

(*) Notice: Subject to any disclaimer, the term of this patent is extended or adjusted under 35 U.S.C. 154(b) by 552 days.

(21) Appl. No.: 12/451,711

(22) PCT Filed: May 28, 2008

(86) PCT No.: PCT/JP2008/060238
§ 371 (c)(1),
(2), (4) Date: Nov. 25, 2009

(87) PCT Pub. No.: WO2008/149868
PCT Pub. Date: Dec. 11, 2008

(65) Prior Publication Data
US 2010/0126249 A1    May 27, 2010

(30) Foreign Application Priority Data
May 31, 2007   (JP) ................. 2007-144737

(51) Int. Cl.
*G01N 29/02* (2006.01)
(52) U.S. Cl.
USPC .......................................... 73/24.01
(58) Field of Classification Search
USPC ........ 73/24.01, 19.03, 649, 1.83, 1.86, 23.25, 73/23.27, 24.04
See application file for complete search history.

(56) References Cited

U.S. PATENT DOCUMENTS

| | | | | |
|---|---|---|---|---|
| 4,220,040 A | * | 9/1980 | Noguchi et al. | 73/24.01 |
| 5,060,514 A | * | 10/1991 | Aylsworth | 73/24.01 |
| 2006/0185443 A1 | | 8/2006 | Fujimoto | |

FOREIGN PATENT DOCUMENTS

| | | | |
|---|---|---|---|
| CN | 1777791 A | | 5/2006 |
| JP | 03-223669 A | | 10/1991 |
| JP | 04-157359 A | | 5/1992 |
| JP | 06-213877 A | | 8/1994 |
| JP | 07-209265 A | | 8/1995 |
| JP | 08-233718 A | | 9/1996 |
| JP | 2002-350410 A | | 12/2002 |
| JP | 2004-317459 A | | 11/2004 |
| JP | 2004317459 A | * | 11/2004 |
| JP | 3610007 B2 | | 1/2005 |
| JP | 3638252 B2 | | 4/2005 |
| JP | 2005-181097 A | | 7/2005 |
| JP | 2006-275608 A | | 10/2006 |

OTHER PUBLICATIONS

PCT/ISA/210, App. No. PCT/JP2008/060238, Sep. 2, 2008 (1 page).

(Continued)

*Primary Examiner* — Peter Macchiarolo
*Assistant Examiner* — Tamiko Bellamy
(74) *Attorney, Agent, or Firm* — Rader, Fishman & Grauer PLLC

(57) ABSTRACT

In an ultrasonic apparatus for measuring the concentration of gas provided with two ultrasonic oscillators for transmitting/receiving an ultrasonic wave, arranged opposite to each other in piping through which a sample gas flows, a temperature sensor, and a pressure sensor, an ultrasonic method and apparatus that can accurately measure gas concentration regardless of pressure of the sample gas are provided as an ultrasonic apparatus for measuring the concentration of gas comprising concentration calculating means for calculating sample gas concentration based on a propagation speed correction coefficient by pressure.

2 Claims, 3 Drawing Sheets

(56) References Cited

OTHER PUBLICATIONS

Sipo, P. R. China, First Office Action, App. No. 200880018174.3, Mar. 23, 2011 (8 pages).

"Cho Onpa Gijutsu Binran", Jun'ichi Saneyoshi et al., Revised New Edition, The Nikkan Kogyo Shinbun, Ltd. (pp. 1165-1189).

Office Action issued in Taiwanese Patent Application No. 097119866, dated Sep. 26, 2013.

\* cited by examiner

ULTRASONIC APPARATUS AND METHOD FOR MEASURING THE CONCENTRATION OF GAS

TECHNICAL FIELD

The present invention relates to an apparatus and method for measuring the concentration of a sample gas by an ultrasonic wave. In more detail, the present invention relates to an apparatus and method for measuring the oxygen concentration of an oxygen concentrated gas fed out of an oxygen concentrator used for medical purpose, for example.

BACKGROUND ART

It is widely known that propagation speed of an ultrasonic wave propagating through a sample gas is represented as a function of concentration and temperature of the sample gas. Supposing that an average molecular weight of the sample gas is M and the temperature is T [k], an ultrasonic propagation speed C [m/sec] in the sample gas is expressed by the following expression (1):

$$C = \sqrt{\frac{kRT}{M}} \qquad \text{[Expression (1)]}$$

Here, k and R are constants (k: Ratio between constant-volume molar specific heat and constant-pressure molar specific heat, R: Gas constant). That is, if the ultrasonic propagation speed C [m/sec] and the temperature T [k] in the sample gas can be measured, the average molecular weight M of the sample gas can be determined. If such sample gas is composed by two components of oxygen and nitrogen, for example, it is known that k=1.4. Supposing that the molecular weight of oxygen is 32 and the molecular weight of nitrogen is 28, the average molecular weight M of the sample gas can be described as $M=32P+28(1-P)$ in a case of oxygen $100 \times P$ [%] ($0 \leq P \leq 1$) and nitrogen $100 \times (1-P)$ [%], and the oxygen concentration P can be determined from the measured average molecular weight M.

Further, supposing that the ultrasonic propagation speed in the sample gas is C [m/sec] and the flow velocity of the sample gas is V [m/sec], since an ultrasonic propagation speed $V_1$ [m/sec] measured when the ultrasonic wave is transmitted in a forward direction to the flow of the sample gas is represented by $V_1=C+V$ and an ultrasonic propagation speed $V_2$ [m/sec] measured when the ultrasonic wave is transmitted in a backward direction to the flow of the sample gas is represented by $V_2=C-V$, the flow velocity V [m/sec] of the sample gas can be acquired by the following expression (2):

$$V = \frac{V_1 - V_2}{2} \qquad \text{[Expression (2)]}$$

By multiplying the flow velocity V [m/sec] of the sample gas obtained as above by an inner area [m²] of piping through which the sample gas flows, a flow rate [m³/sec] of the sample gas can be obtained. Moreover, by volume conversion or time conversion, the flow rate can be easily obtained in [L/min].

Various apparatuses and methods for measuring the concentration and flow rate of the sample gas from the propagation speed or propagation time of an ultrasonic wave propagating through the sample gas using the above principle have been proposed. For example, Japanese Patent Laid-Open Publication No. H6-213877 describes an apparatus for measuring the concentration and flow rate of the sample gas by arranging two ultrasonic oscillators in the piping through which the sample gas flows opposite to each other and by measuring the propagation time of the ultrasonic wave propagating between the ultrasonic oscillators. In addition, Japanese Patent Laid-Open Publication No. H7-209265 and Japanese Patent Laid-Open Publication No. H8-233718 describe an apparatus for measuring the concentration of the sample gas by measuring the propagation speed or propagation time of the ultrasonic wave propagating through a sensing area in a sonic wave reflection method using a single ultrasonic oscillator.

DISCLOSURE OF THE INVENTION

In order to accurately measure the concentration of the sample gas using such propagation speed of the ultrasonic wave and the like, an accurate propagation speed of the ultrasonic wave considering influencing factors in the piping through which the sample gas flows should be known.

As a treatment method for disorders in respiratory organs such as asthma, emphysema, chronic bronchitis and the like, an oxygen inhalation therapy in which a patient inhales an oxygen gas or oxygen-enriched air, and as its oxygen supply source, there is known a pressure-fluctuation adsorption type oxygen concentrator that concentrates oxygen existing in the air in approximately 21% to high concentration and supplies it to a user. Such pressure-fluctuation adsorption type oxygen concentrator is an apparatus for adsorbing nitrogen in a pressurized condition and taking out unadsorbed oxygen as an oxygen concentrated gas using an adsorbent bed filled with molecular seive zeolite of 5A type, 13X type, Li—X type, MD-X type and the like as an adsorbent that selectively adsorbs nitrogen rather than oxygen and supplying compressed air from a compressor to the adsorbent bed. Such an apparatus is usually provided with two or more adsorbent beds, and by conducting a pressurized adsorption process for having nitrogen adsorbed by the adsorbent so as to generate unadsorbed oxygen at one of the adsorption beds and a desorption regeneration process in which pressure of the other adsorption bed is reduced so as to exhaust adsorbed nitrogen for regeneration while sequentially switching them, oxygen can be generated continuously.

In the pressure-fluctuation adsorption type oxygen concentrator, since oxygen is continuously generated by switching the pressurized adsorption process and the desorption regeneration process in the piping, and a flow rate of supplied oxygen is also used in switching at any time, pressure of the sample gas in the piping is fluctuated. However, change in the propagation speed of the ultrasonic wave by pressure is not considered at all in usual, which is a factor to deteriorate an accuracy of measurement values of the sample gas concentration.

The present invention has an object to provide an ultrasonic method for measuring the concentration of sample gas that can accurately measure the sample gas concentration by pressure by deriving a coefficient for correcting the propagation speed accompanying the pressure of the sample gas and an apparatus using it.

As the result of keen examination by the inventors in order to achieve the above object, they have found that the sample gas concentration can be accurately measured by changing the pressure in the piping through which the sample gas flows is changed at each temperature, calculating a propagation speed correction coefficient, expressing the propagation speed correction coefficient as a function of the temperature, and correcting the propagation speed.

That is, the present invention provides an ultrasonic apparatus for measuring the concentration of gas comprising two ultrasonic oscillators for transmitting/receiving an ultrasonic wave, arranged opposite to each other in the piping through which the sample gas flows, a temperature sensor, and a pressure sensor, characterized in that concentration calculation means for calculating the concentration of the sample gas based on the propagation speed correction coefficient by the pressure of the sample gas.

Further, the present invention provides an ultrasonic apparatus for measuring the concentration of gas characterized in that such concentration calculation means is means for correcting a propagation time till the ultrasonic oscillators receive the ultrasonic wave using the propagation speed correction coefficient according to the measured temperature and the measured pressure of the sample gas and correcting a propagation speed C till the ultrasonic oscillators receive the ultrasonic wave by the following expression (3):

$$C = \sqrt{\frac{kRT}{M}\left(1 + \frac{P}{RT}B(T) + \left(\frac{P}{RT}\right)^2 C(T) + \ldots\right)}$$ [Expression (3)]

Where, k: ratio between constant-volume molar specific heat and constant-pressure molar specific heat, R: gas constant, T: measured temperature of sample gas, M: average molecular weight of sample gas, P: measured pressure of sample gas, and B(T), C(T): propagation speed correction coefficients.

Furthermore, the present invention provides an ultrasonic method for measuring the concentration of gas, in a method for measuring the concentration of a sample gas based on a propagation time till an ultrasonic wave transmitted from ultrasonic oscillators for transmitting/receiving the ultrasonic wave arranged opposite to each other in piping through which the sample gas flows is received by the ultrasonic oscillator arranged on the opposite side, characterized in that the propagation time till the ultrasonic oscillator receives the ultrasonic wave based on a propagation speed correction coefficient according to the temperature and the pressure of the sample gas is corrected, and particularly characterized in that the propagation speed C till the ultrasonic oscillator receives the ultrasonic wave is corrected.

Moreover, the present invention provides an ultrasonic method for measuring concentration characterized in that propagation speed correction coefficients (B(Ta), C(Ta)) at a temperature Ta is acquired from ultrasonic propagation speeds of the plural sample gases with different pressures at the temperature Ta and the propagation speed is corrected based on a function of the temperature T of the propagation speed correction coefficient.

BEST MODE FOR CARRYING-OUT OF THE INVENTION

An embodiment of an ultrasonic method for measuring the concentration and flow rate of gas of the present invention will be described below. In this embodiment, an apparatus for measuring oxygen concentration of a sample gas composed by three components of oxygen, nitrogen, and argon or two components of oxygen and nitrogen will be described. The sample gas that can be measured by the present invention is not limited to the sample gas composed by oxygen, nitrogen, and argon shown in this embodiment, but the present invention can be easily applied to a gas composed by other molecules.

Figure 1:
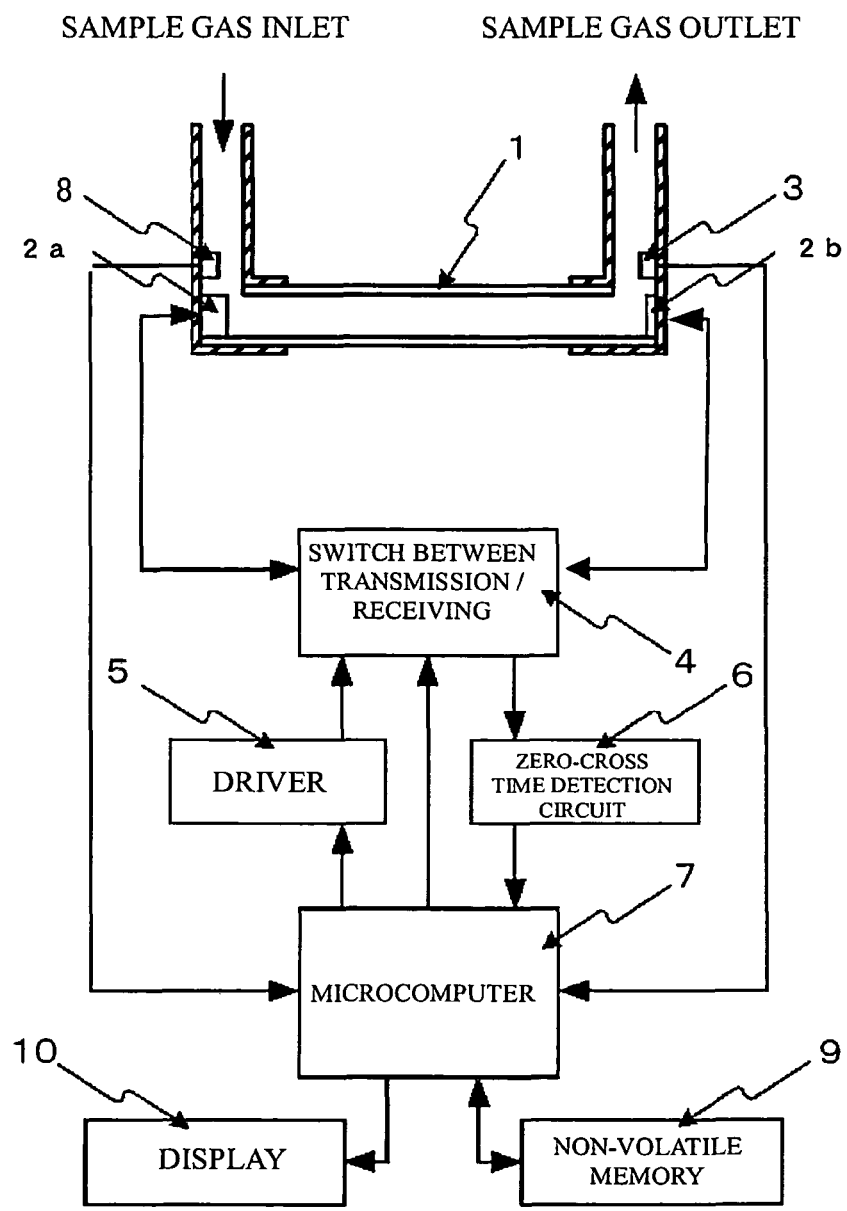
FIG. 1 is an outline diagram illustrating configuration of an ultrasonic apparatus for measuring the concentration of oxygen of the present invention.

Configuration of the ultrasonic means for measuring the oxygen concentration and flow rate of gas is shown in FIG. 1. In piping 1 through which the sample gas flows, two ultrasonic oscillators 2 (first ultrasonic oscillator 2a and second ultrasonic oscillator 2b) are arranged opposite to each other, and a switch 4 for switching transmission/receiving of the ultrasonic oscillators 2, a driver 5 for transmitting an ultrasonic transmission pulse to the ultrasonic oscillators 2, a zero-cross time detection circuit 6 for detecting zero-cross time in an ultrasonic receiving waveform, a microcomputer 7 for calculating a concentration, flow rate of the sample gas, a temperature sensor 3 for measuring a temperature of the sample gas in the piping 1, a pressure sensor 8 for measuring a pressure in the piping in the piping 1, and a non-volatile memory 9 in which the propagation speed correction coefficient is stored are provided. A display 10 displays the concentration of the measured sample gas. As long as a flow of the sample gas is not disturbed, the temperature sensor and the pressure sensor may be arranged at the center on an ultrasonic propagation path.

A method for measuring the concentration of a sample gas using the above apparatus configuration will be described. It is widely known that the propagation speed of the ultrasonic wave propagating through the sample gas is expressed as a function of the concentration and temperature of the sample gas. That is, supposing that an average molecular weight of the sample gas is M and the temperature is T [K], an ultrasonic propagation speed C [m/sec] in the sample gas is expressed by the above expression (1). If an influence of the pressure is not considered as in the expression (1) or if the pressure in the piping is zero, an accurate oxygen concentration of the sample gas flowing through the piping can be measured by this method. However, if a pressure is present in the piping, it is impossible to derive an accurate measured value of the oxygen concentration.

Figure 2:
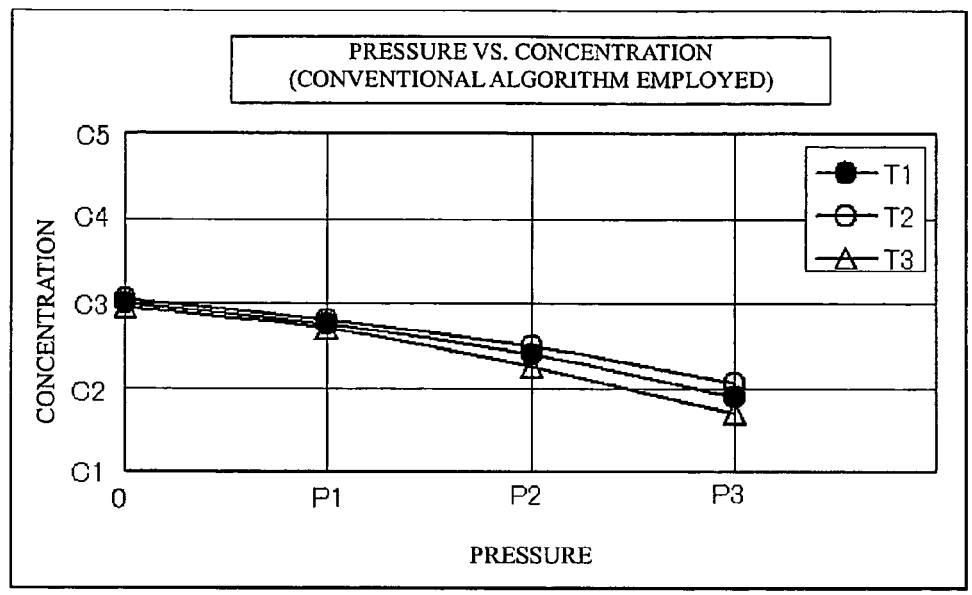
FIG. 2 shows a relation between an oxygen concentration value and a pressure of a conventional ultrasonic apparatus for measuring the concentration of oxygen.

A result of the oxygen concentration in the sample gas derived by a measuring method using a conventional algorithm not considering the pressure as described in Japan Patent Laid-Open Publication No. 2004-317459 is shown in FIG. 2. As shown in FIG. 2, since the propagation speed of the ultrasonic wave depends on the pressure, it is known that an output value of the oxygen concentration is lowered as the pressure rises.

The fact that the ultrasonic propagation speed C depends on the pressure and is expressed as a function of the temperature is generally known and can be expressed by an expression (3):

$$C = \sqrt{\frac{kRT}{M}\left(1 + \frac{P}{RT}B(T) + \left(\frac{P}{RT}\right)^2 C(T) + \ldots\right)} \quad \text{[Expression (3)]}$$

Here, P [N/m²] indicates an output value of the pressure sensor built in the ultrasonic apparatus for measuring the concentration of sample gas according to the present invention. B(T) and C(T) [m³/mol] indicate ultrasonic propagation speed correction coefficients.

In this embodiment, up to the term of B(T) is applied and shown by using the following expression (4):

$$C = \sqrt{\frac{kRT}{M}\left(1 + \frac{P}{RT}B(T)\right)} \quad \text{[Expression (4)]}$$

Figure 5:
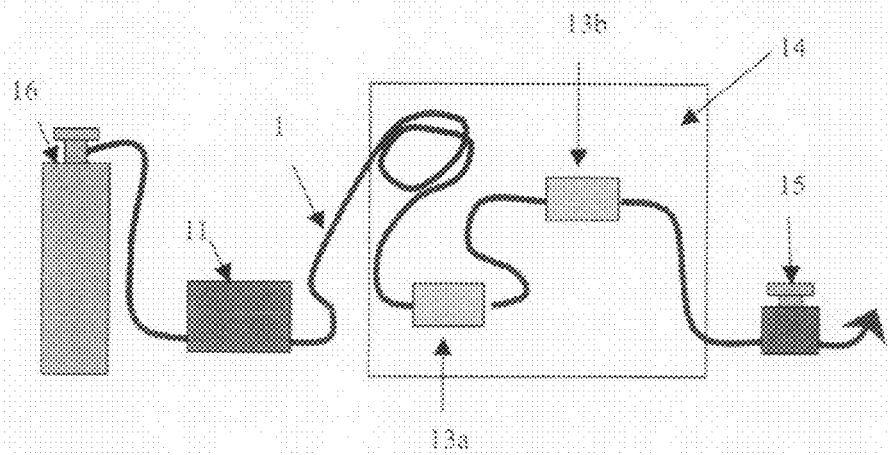
FIG. 5 shows a testing device for acquiring the propagation speed correction coefficient of an embodiment.

One of calculating methods of the propagation speed correction coefficient will be illustrated. As shown in FIG. 5, a plurality of ultrasonic apparatuses 13a, 13b for measuring the concentration of sample gas are installed inside a device 14 capable of temperature adjustment such as a constant-temperature bath, for example. A gas bomb 16 installed outside is connected to the ultrasonic apparatuses 13a, 13b for measuring the concentration of sample gas through a flow-rate adjuster 11. In order to stabilize the temperature so that the sample gas temperature matches a set temperature of the constant-temperature bath, a length of a tube 12 in the constant-temperature bath up to the ultrasonic apparatuses 13a, 13b for measuring the concentration of sample gas is made longer. The tube coming out of the constant-temperature bath 14 is connected to a pressure regulating valve 15 so that a pressure value can be adjusted.

By using such pressure regulating valve 15, two types of pressure conditions $P_1$, $P_2$ are prepared, and by measuring ultrasonic propagation speeds C1 and C2 at a given stable temperature $T_1$ in each condition, average molecular weights $M_1$, $M_2$ of the sample gas can be acquired by the following expressions (5), (6). However, temperature conditions in the two types of pressure standards do not necessarily have to be matched.

$$M_1 = \frac{kRT}{C_1^2}\left(1 + \frac{P_1}{RT_1}B(T_a)\right) \quad \text{[Expression (5)]}$$

$$M_2 = \frac{kRT_1}{C_2^2}\left(1 + \frac{P_2}{RT_1}B(T_a)\right) \quad \text{[Expression (6)]}$$

If the sample gas at actual measurement is the same, M1=M2, and the propagation speed correction coefficient B(Ta) can be calculated.

Figure 3:
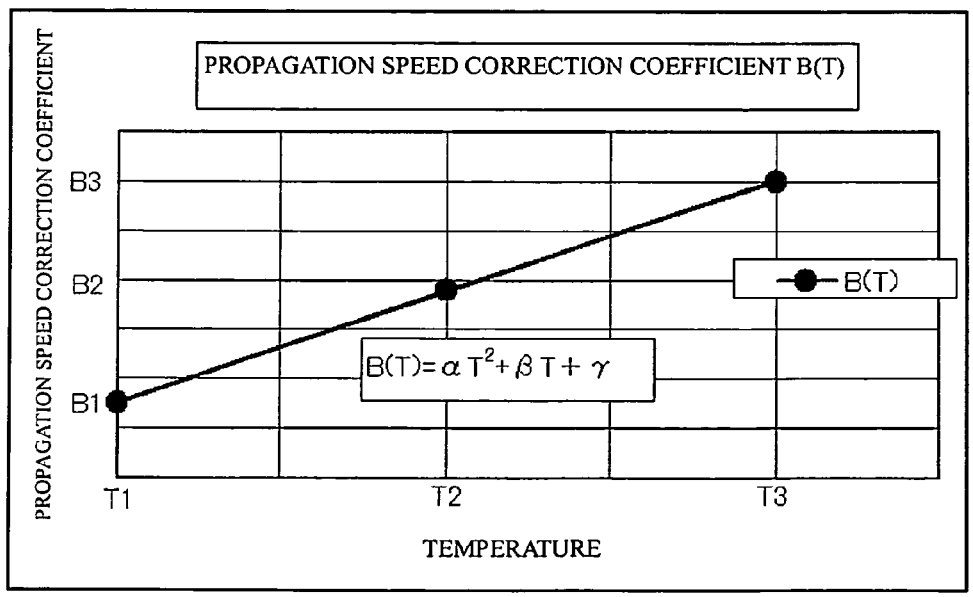
FIG. 3 shows a relation between a propagation speed correction coefficient and a temperature.

The propagation speed correction coefficients $B_2$, $B_3$ at the other temperatures $T_2$, $T_3$ and the like are also acquired by the similar method, and a relation between the propagation correction coefficients ($B_1 \sim B_3$) and the temperatures ($T_1 \sim T_3$) including the propagation speed correction coefficient B(Ta)=$B_1$ at the temperature $T_1$ is plotted in FIG. 3.

Here, by approximating the plotted points by a second-order approximation curve, as shown in the following expression (7), the propagation correction coefficient B (T) can be acquired as a function of the temperature (T). However, the approximation curve does not necessarily have to be a second-order curve.

$$B(T) = \alpha T^2 + \beta T \quad \text{[Expression (7)]}$$

Figure 4:
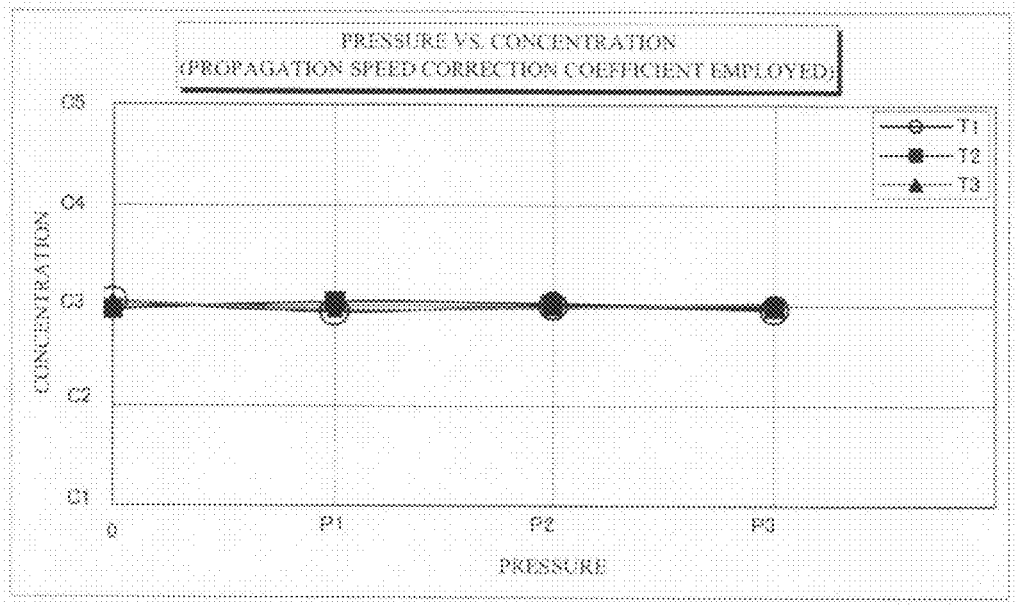
FIG. 4 shows a relation between the oxygen concentration value and the pressure of the ultrasonic apparatus for measuring the concentration of oxygen for which the propagation speed correction coefficient of the present invention is employed.

A result of measurement of the concentration of the sample gas by the ultrasonic propagation speed by substituting an output value of the temperature sensor and the output value of the pressure sensor into the expression (7) and the expression (4) for correction is shown in FIG. 4. As shown in FIG. 4, the oxygen concentration is not affected by pressure fluctuation, but accurate concentration measurement can be made.

Effect of the Invention

By using the method of the present invention, there can be provided an ultrasonic method for measuring the concentration of sample gas and an apparatus for measuring the concentration of gas that can accurately measure the sample gas concentration by pressure by deriving a coefficient for correcting the propagation speed accompanying the pressure of the sample gas.

The invention claimed is:

1. An ultrasonic method for measuring the concentration of a specific component gas in a sample gas based on a propagation time till an ultrasonic wave transmitted from two ultrasonic transducers transmitting/receiving the ultrasonic wave, arranged opposite to each other in piping through which the sample gas flows, is received by the ultrasonic transducer arranged on the opposite side, the method comprising steps of:

measuring a propagation time till the ultrasonic wave transmitted from each of the two ultrasonic transducers is received by the other ultrasonic transducer;
measuring a sample gas temperature
measuring a sample gas pressure; and
correcting the propagation time till the ultrasonic transducer receives the ultrasonic wave based on a propagation speed correction coefficient according to the temperature and pressure of the sample gas, wherein
the step for correcting the propagation time till the ultrasonic transducer receives the ultrasonic wave is a step for correcting a propagation speed (C) of the ultrasonic wave by the following expression:

$$C = \sqrt{\frac{kRT}{M}\left(1 + \frac{P}{RT}B(T)\right)}$$

where k: ratio between constant-volume molar specific heat and constant-pressure molar specific heat, R: gas constant, T: measured temperature of sample gas, M: average molecular weight of sample gas, P: measured pressure of sample gas, B(T): propagation speed correction coefficients, and the propagation speed correction coefficient B(T) is acquired as an approximate function of the measured temperature T calculated from an ultrasonic propagation speed C at a given temperature T under different pressure conditions, measured from an ultrasonic propagation time till the ultrasonic wave transmitted from the two ultrasonic transducers transmitting/receiving the ultrasonic wave and wherein B(T)=$\alpha T^2 + \beta T + \gamma$ where $\alpha$, $\beta$ and $\gamma$ are constants.

2. An ultrasonic apparatus for measuring a concentration of gas comprising piping extending along an axis and through which a target gas to be measured flows, a first ultrasonic transducer arranged inside the piping for transmitting/receiving an ultrasonic wave, a second ultrasonic transducer arranged inside the piping and opposed to the first ultrasonic transducer for transmitting/receiving the ultrasonic wave, a transmission/receiving switch for switching control an ultrasonic transmission mode in which the ultrasonic wave is transmitted from the ultrasonic transducer and an ultrasonic receiving mode in which the transmitted ultrasonic wave is received between the first and second ultrasonic transducers, a temperature sensor arranged at the piping for measuring a temperature of the target gas, and a pressure sensor arranged at the piping for measuring a pressure of the target gas, wherein concentration calculating means for calculating the concentration of the target gas is provided based on a propagation speed correction coefficient by a propagation time till the ultrasonic wave transmitted from each of the two ultrasonic transducers is received by the other ultrasonic transducer, an output value of the temperature sensor, and a pressure value of the pressure sensor;

wherein the concentration calculating means is provided with means for correcting a propagation speed (C) of the ultrasonic wave by the following expression:

$$C = \sqrt{\frac{kRT}{M}\left(1 + \frac{P}{RT}B(T)\right)}$$

where k: ratio between constant-volume molar specific heat and constant-pressure molar specific heat, R: gas constant, T: measured temperature of sample gas, M: average molecular weight of sample gas, P: measured pressure of sample gas, B(T): propagation speed correction coefficient, and means for correcting a propagation speed based on a function of a temperature T of the propagation speed correction coefficient by acquiring a propagation speed correction coefficient wherein the propagation speed correction coefficient B(T) is acquired as an approximate function of the measured temperature T calculated from an ultrasonic propagation speed C at a given temperature T under different pressure conditions, measured from an ultrasonic propagation time till the ultrasonic wave transmitted from the two ultrasonic transducers transmitting/receiving the ultrasonic wave; and wherein $B(T)=\alpha T^2+\beta T+\gamma$ where $\alpha$, $\beta$ and $\gamma$ are constants.

* * * * *